(12) United States Patent
Thors et al.

(10) Patent No.: US 12,036,020 B2
(45) Date of Patent: Jul. 16, 2024

(54) NON-INVASIVE MONITORING SYSTEM

(71) Applicant: AERBETIC, INC., Birmingham, AL (US)

(72) Inventors: Arnar Thors, Birmingham, AL (US); Eric Housh, Birmingham, AL (US); Lloyd Cooper, Birmingham, AL (US); Matt Fitzgerald, Birmingham, AL (US)

(73) Assignee: AERBETIC, INC., Birmingham, AL (US)

( * ) Notice: Subject to any disclaimer, the term of this patent is extended or adjusted under 35 U.S.C. 154(b) by 574 days.

(21) Appl. No.: 17/294,279

(22) PCT Filed: Nov. 14, 2019

(86) PCT No.: PCT/US2019/061530
§ 371 (c)(1),
(2) Date: May 14, 2021

(87) PCT Pub. No.: WO2020/102573
PCT Pub. Date: May 22, 2020

(65) Prior Publication Data
US 2022/0007972 A1    Jan. 13, 2022

Related U.S. Application Data

(60) Provisional application No. 62/760,981, filed on Nov. 14, 2018.

(51) Int. Cl.
*A61B 5/1477* (2006.01)
*A61B 5/00* (2006.01)
*A61B 5/145* (2006.01)

(52) U.S. Cl.
CPC ........ *A61B 5/1477* (2013.01); *A61B 5/14546* (2013.01); *A61B 5/746* (2013.01)

(58) Field of Classification Search
CPC ..... A61B 5/083; A61B 5/097; A61B 5/14517; A61B 5/14532; A61B 5/14546;
(Continued)

(56) References Cited

U.S. PATENT DOCUMENTS

| 8,652,040 B2 | 2/2014 | Leboeuf et al. |
| 2015/0157261 A1 | 6/2015 | Sakagami |

(Continued)

FOREIGN PATENT DOCUMENTS

| CN | 104316573 A | 1/2015 |
| EP | 2762880 B1 | 8/2014 |
| JP | H0634590 A | 2/1994 |

OTHER PUBLICATIONS

D. A. P. Daniel, K. Thangavel and K. T. Rajakeerthana, "Empirical study on early detection of lung cancer using breath analysis," 2015 International Conference on Innovations in Information, Embedded and Communication Systems (ICIIECS), Coimbatore, India , 2015, pp. 1-6 (Year: 2015).*

(Continued)

*Primary Examiner* — Eric J Messersmith
(74) *Attorney, Agent, or Firm* — Jake M. Gipson; Bradley Arant Boult Cummings LLP

(57) ABSTRACT

A wearable device for non-invasive monitoring of the presence, amount, and/or concentration of an analyte in a sample from a user of the device is described. The analyte is selected to be indicative of or related to a physiological status of a user. Relevant physiological status include hypoglycemia, infection, respiratory infection, urinary infection, gastrointestinal infection, obesity, diabetes, type I diabetes and type II diabetes.

21 Claims, 5 Drawing Sheets

(58) Field of Classification Search
CPC ..... A61B 5/1477; A61B 5/4866; A61B 5/681; A61B 5/746; C11D 1/143; C11D 1/72; C11D 1/83; C11D 11/0029; C11D 11/0047; C11D 3/0047; C11D 3/2079; C11D 3/2086; C11D 3/362; H01L 21/02041
See application file for complete search history.

(56) References Cited

U.S. PATENT DOCUMENTS

| | | | |
|---|---|---|---|
| 2016/0174853 | A1 | 6/2016 | Cho et al. |
| 2017/0215795 | A1* | 8/2017 | Ahmad ................ A61B 5/7455 |
| 2017/0325724 | A1 | 11/2017 | Wang et al. |
| 2018/0132783 | A1 | 5/2018 | Wang et al. |

OTHER PUBLICATIONS

S. Lekha and S. M., "Real-Time Non-Invasive Detection and Classification of Diabetes Using Modified Convolution Neural Network," in IEEE Journal of Biomedical and Health Informatics, vol. 22, No. 5, pp. 1630-1636, Sep. 2018 (Year: 2018).*

European Search Report dated Jun. 27, 2022 for European Patent Application No. 19885133.9.

Souvik Das, Significance of Exhaled Breath Test in Clinical Diagnosis: A Special Focus on the Detection of Diabetes Mellitus, J.Me. Biol. Eng., 2016, 36, pp. 605-624, DOI 10.1007/s40846-016-0164-6.

Jan Hendrik Leopold, Glucose prediction by analysis of exhaled metabolites a systematic review, BMC Anesthesiology, 2014, 14:46, pp. 1-9, http://www.biomedicalcentral.com/1471-2253/14/46.

Yoko Iizuka, Development of monitoring system of noninvasive blood sugar by skin gas measurement, Medical device development promotion research project, 2014 commissioned business progress report, Mar. 2015, pp. 1-17.

Takaharu Kondo, Bio-gas analysis for diagnosis of diseases, Journal of Japan Association on Odor Environment, 2017, vol. 48, No. 6, pp. 402-409.

Kumamoto University, Highly sensitive gas sensors for volatile organic compound detection, EurekAlert!, News Release, Feb. 1, 2017, https://www.eurekalert.org/news-releases/716894?language=japanese.

Office action dated Apr. 11, 2023 for patent application serial No. JP 2021-526443 and English translation.

* cited by examiner

NON-INVASIVE MONITORING SYSTEM

CROSS-REFERENCE TO RELATED APPLICATIONS

This application is a national stage under 35 U.S.C. 371 of International Application No. PCT/US2019/061530 having an international filing date of Nov. 14, 2019 (currently published), which claims priority to U.S. Provisional Patent Application No. 62/760,981 filed on Nov. 14, 2018.

BACKGROUND

Many individual suffer from a variety of diseases and conditions that require routine monitoring of an analyte (such as, without limitation, determining the concentration of the analyte). For example, there is a growing increase in the prevalence of diabetic conditions, including both type I and type II diabetes. Such patients, for example, may be required to monitor an analyte in the blood, for example the presence of glucose or the concentration of glucose in the blood.

The prior art has hypothesized that the amount or concentration of certain analytes, particularly volatile organic compounds (VOCs), can indicate that a subject is suffering from or likely to suffer from a given disease or condition. The results of such approaches are not conclusive, however, with some studies reporting a correlation between one or more analytes and a given disease or condition and other studies reporting no correlation. As one example, consider a subject with type 1 diabetes. In order to adequately manage type I diabetes, the subject is required to monitor blood glucose concentrations accurately. If blood glucose concentrations are too high (hyperglycemia) or too low (hypoglycemia), corrective action on the part of the subject must be taken to avoid serious consequences. Hypoglycemia can result in seizures, coma, and even death. By monitoring (for example, determining the concentration of) one or more analytes, such as one or more VOCs, associated with hypoglycemia, a subject may be alerted that he/she is suffering from, likely to suffer from, or in danger of suffering from hypoglycemia and take needed corrective action.

An increasingly large percentage of total healthcare spending is allocated to the care and treatment of subjects with such conditions. In particular, healthcare costs are rising for those individuals that do not adequately monitor their conditions (for example, a person with type I diabetes who fails to adequately monitor glucose concentrations). One reason for failure to comply with monitoring of such conditions is that monitoring is painful (for example, a finger stick), is difficult to accomplish, requires the user to initiate the process and/or requires special equipment that must be transported with the user. In addition, in many cases such monitoring, with all the attendant inconveniences, must frequently be repeated at intervals during the day/night. Therefore, the devices and methods of the prior art suffer from drawbacks and shortcomings that result in decreased monitoring.

The present disclosure provides a solution to the problems of the prior art by providing a device to accurately and conveniently monitor the presence of one or more analytes originating from a subject.

SUMMARY OF THE DISCLOSURE

The present disclosure provides a wearable device for non-invasive monitoring of the presence, amount, and/or concentration of an analyte in a sample from a user of the device. In certain embodiments, the analyte is indicative of or related to a physiological status of a user. In certain embodiments, the analyte indicates the subject is suffering from, likely to suffer from, or in danger of suffering from a disease or condition.

In a first aspect, the present disclosure provides a wearable device for non-invasive monitoring of an analyte in a sample from a user of the device.

In a second aspect, the present disclosure provides a wearable device for non-invasive monitoring of an analyte in a sample from a user of the device wherein the device analyzes the sample to determine the presence, amount, and/or concentration of the analyte.

In a third aspect, the present disclosure provides a wearable device for non-invasive monitoring of an analyte in a sample from a user of the device wherein the device analyzes the sample to determine the presence, amount, and/or concentration of the analyte and alerts the user to a result of such analysis.

In a fourth aspect, the present disclosure provides for devices, systems and methods that accurately determine and/or report the presence, concentration and/or amount of an analyte in a sample from a user.

In a fifth aspect, the present disclosure provides for a method of evaluating a physiological status of a user by non-invasive monitoring of an analyte in a sample from the user, the method comprising: a) providing a wearable device of the present disclosure wherein the user wears the device; b) exposing the wearable device to a sample from the user; c) analyzing the sample to determine the presence, amount and/or concentration of an analyte to produce a result; d) and optionally (i) providing the result to the user; (ii) alerting the user of the result; and/or (iii) notifying the user if the result is within an acceptable range or outside of an acceptable range for the physiological status.

In a sixth aspect, the present disclosure provides for a method for determining if a user is suffering from, likely to suffer from, or in danger of suffering from a disease or condition by non-invasive monitoring of an analyte in a sample from the user, the method comprising: a) providing a wearable device of the present disclosure wherein the user wears the device; b) exposing the wearable device to a sample from the user; c) analyzing the sample to determine the presence, amount and/or concentration of an analyte to produce a result; d) and optionally (i) providing the result to the user; (ii) alerting the user of the result; and/or (iii) w notifying the user if the result is within an acceptable range or outside of an acceptable range for the disease of condition.

In any of the first to sixth aspects, the non-invasive monitoring is accomplished without requiring the user to provide a direct sample to the device (for example, exhaling directly into the device).

In any of the first to sixth aspects, the non-invasive monitoring is accomplished without requiring the user to exhale into the device to initiate the monitoring process, to complete the monitoring process, determine a result of the monitoring process, and/or view such results.

In any of the first to sixth aspects, the non-invasive monitoring is accomplished without requiring an action of the user to initiate the monitoring process, to complete the monitoring process, determine a result of the monitoring process, and/or view such results.

In any of the first to sixth aspects, the analyte is indicative of or related to a physiological status of a user (such as, but not limited to, hypoglycemia).

In any of the foregoing embodiments, the physiological status is hypoglycemia. In any of the foregoing embodiments, the physiological status is an infection. In any of the foregoing embodiments, the physiological status is a respiratory infection. In any of the foregoing embodiments, the physiological status is a urinary infection. In any of the foregoing embodiments, the physiological status is a gastrointestinal infection. In any of the foregoing embodiments, the physiological status is obesity. In any of the foregoing embodiments, the physiological status is diabetes. In any of the foregoing embodiments, the physiological status is type I diabetes. In any of the foregoing embodiments, the physiological status is type II diabetes.

In any of the first to sixth aspects, the analyte is associated with a disease or condition and can be used to determine if a user is suffering from, likely to suffer from, or in danger of suffering from a disease or condition.

In any of the first to sixth aspects, a result is provided to the user. In certain embodiments, the result is the presence, concentration and/or amount of the analyte. In certain embodiments, the result is the presence of the analyte. In certain embodiments, the result is the concentration of the analyte. In certain embodiments, the result is the amount of the analyte.

In any of the first to sixth aspects, the use of the wearable device reduces the risk of user non-compliance, thereby decreasing the possibility of non-compliance by a user (whether intentional or unintentional).

In any of the first to sixth aspects, the wearable device comprises i) a housing; ii) an inlet port; iii) a chamber in the interior of the housing; iv) an inlet passage having a first end in fluid communication with the inlet port and a second end in fluid communication with the chamber; v) a sensor system; and vi) a controller in communication with the sensor system. The wearable device may further comprise one or more of the following components: a wireless communication module, a membrane (such as a membrane to cover one or more of the inlet ports and/or exit ports), an exit port, a pump assembly, a user input, and a notification module.

In any of the first to sixth aspects, the wearable device comprises i) a housing; ii) a plurality of inlet ports; iii) a chamber in the interior of the housing; iv) an inlet passage for each inlet port, each inlet passage having a first end in fluid communication with its inlet port and a second end in fluid communication with the chamber; v) a sensor system; and vi) a controller in communication with the sensor system. The wearable device may further comprise one or more of the following components: a wireless communication module, a membrane (such as a membrane to cover one or more of the inlet ports and/or exit ports), an exit port, a pump assembly, a user input, and a notification module.

DETAILED DESCRIPTION

Definitions

Figure 1:
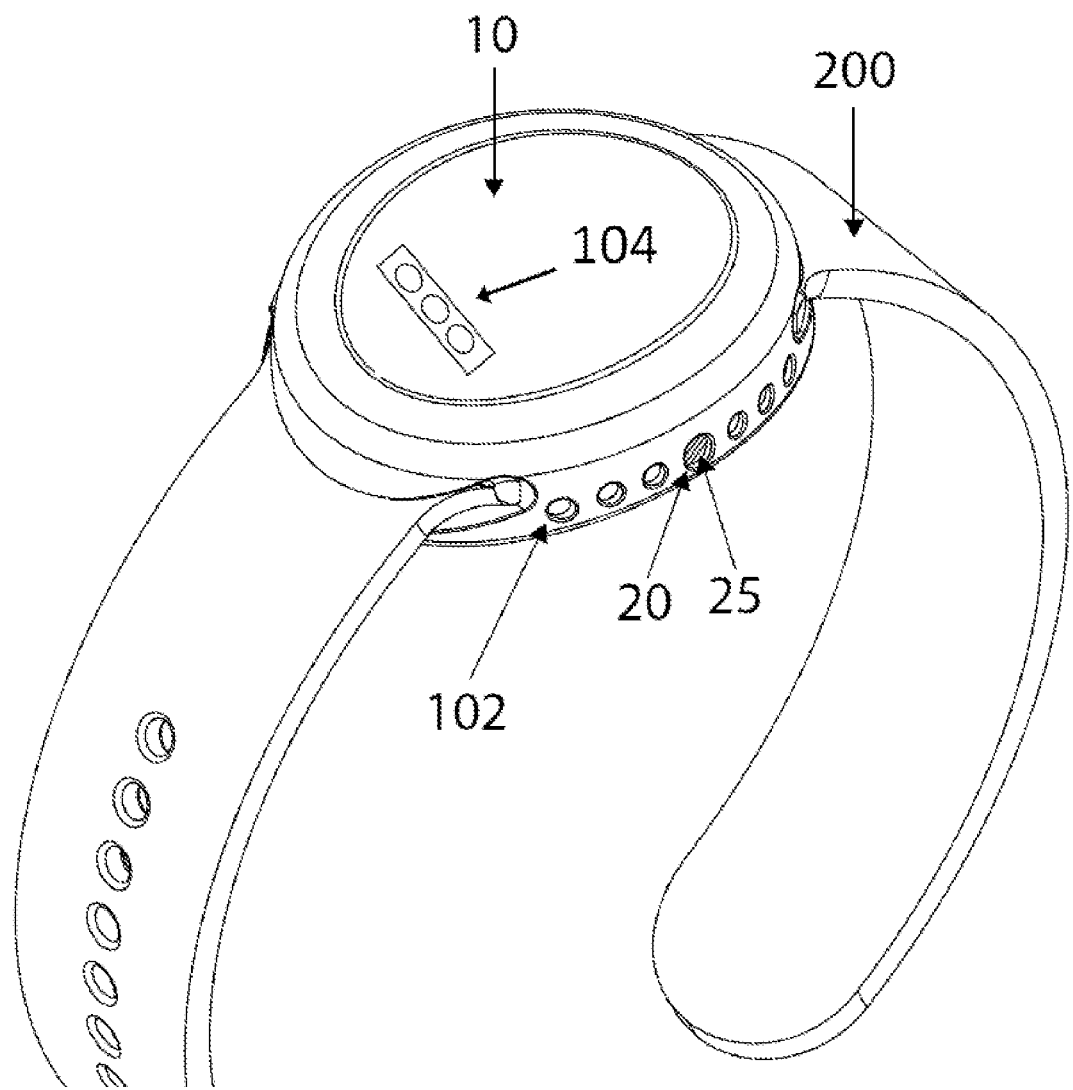
FIG. 1 shows an exterior view of one embodiment of the wearable device of the present disclosure.

All of the actions described herein as being performed by an "electronic device" may be performed under the control of a mobile application, such as program contained on a smart phone or smart watch.

All of the methods and tasks described herein may be performed and fully automated by a computer system. The computer system may, in some cases, include multiple distinct computers or computing devices (including, but not limited to, physical servers, workstations, storage arrays, and cloud computing resources) that communicate and interoperate over a network to perform the described functions. Each such computing device typically includes one or more processors for execution of program instructions stored in a memory or other non-transitory computer-readable storage medium (including, but not limited to, a solid-state storage device, disk drives, thumb drive and the like). The functions disclosed herein may be embodied in program instructions. The various functions disclosed herein may be implemented in application-specific circuitry of the system. Where the computer system includes multiple computing devices, these devices may, but need not, be co-located. In certain embodiments, a result of the disclosed methods and/or tasks may be persistently stored by transforming physical storage devices, including those described herein, into a different state. In some embodiments, the computer system may be a cloud-based computing system.

The functions described herein may be carried out using an algorithm designed for accomplishing such function. The algorithm may be a part of a processor of a device of the present disclosure (in particular, a wearable device) or a part of a processor of a computer system described herein. Depending on the embodiment, the functions of any method processes or algorithms described in the present disclosure can be performed in a different sequence from that disclosed. Moreover, in certain embodiments, the functions described herein can be performed concurrently, for example, through multi-threaded processing, interrupt processing, or multiple processors or processor cores or on other parallel architectures. In certain embodiments, the functions described herein can be performed sequentially.

The illustrative logical blocks, modules, routines, and algorithm steps described in the present application can be implemented as electronic hardware (e.g., ASICs or FPGA devices), computer software that runs on general purpose computer hardware, or combinations of both. For example, various illustrative components, blocks, modules, and steps have been described above generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as limiting the present disclosure to such implementation.

The illustrative logical blocks, modules, routines, and algorithm steps described in the present application can be implemented by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination of the foregoing. A general purpose processor device can be a microprocessor, but in the alternative, the processor device can be a controller, microcontroller, or state machine, or combinations of the foregoing. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

The terms "comprising," "including," "having," and the like are synonymous and are used inclusively, in an open-ended fashion, and do not exclude additional elements, features, acts, operations, and so forth.

The term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z).

The present disclosure provides a solution to the shortcomings of the prior art by providing a wearable device that non-invasively monitors the presence, amount and/or concentration of an analyte emanating from or derived from a user. In certain embodiments, the presence, amount and/or concentration of the analyte is indicative of or related to a physiological status of the user. In certain embodiments, the presence, amount and/or concentration of the analyte is used to determine if a user is suffering from, likely to suffer from, or in danger of suffering from a disease or condition. In particular, the present disclosure provides a solution to the shortcomings of the prior art by providing a wearable device that non-invasively monitors (for example, analyzing a sample to determine the presence, amount and/or concentration of) an analyte emanating from or derived from a user, wherein the non-invasive monitoring is accomplished without requiring any action on the part of the user to initiate the monitoring process, to complete the monitoring process, determine a result of the monitoring process, and/or view such results.

Sample

The sample may be any gas or fluid that contains an analyte derived from or emanating from the user of the wearable device. In one embodiment, the sample is an indirect sample. An indirect sample is a sample that is not introduced directly into the device by a user (for example, a user breathing through a tube into an inlet port of the device). In one embodiment, the sample is co-mingled with the ambient environment of the user (for example, ambient air) before being introduced into the device. In a particular embodiment, the sample is ambient air that surrounds the wearable device and the user. When the sample is ambient air, the analyte originates from or is derived from the user of the wearable device and becomes mixed with ambient air such that the target analyte is contained in the ambient air surrounding the user. For example, a user of the wearable device may exhale the analyte in breath, excrete the analyte though skin (VOCs are volatile at body temperature), excrete the analyte through perspiration, excrete the analyte through eccrine glands, apocrine glands, and/or sebaceous glands, or any combination of the foregoing, such that the analyte is mixed with the ambient air.

In certain embodiments, the sample may be a direct sample meaning that the user directly introduces the sample into the device. A direct sample may be useful for calibrating the device or may be required when the user is in an environment where an indirect sample is not feasible (for example, when the user is in a closed environment with a high concentration of VOCs or other compounds that interfere with the detection of the analyte).

In certain embodiments, the sample is ambient air containing an analyte emanating from the user (for example, an analyte contained in an exhaled breath or excreted from the user). In certain embodiments, the sample is exhaled breath. In certain embodiments the sample is exhaled breath and the sample is directly introduced into the device by the user (for example, the user exhales a breath directly into an inlet port of the device).

Analytes and Volatile Organic Compounds

Humans and animals emit a mixture of many different types of compounds, including VOCs, lipids, peptides, and other compounds. In a preferred embodiment, the analyte is a VOC. The composition of emitted compounds, particularly VOCs, can differ between healthy individuals and individuals with a specific disease or condition and can be indicative or related to a given physiological status of the user.

In one embodiment, the analyte is present in the sample at a concentration greater than or equal to 1 part per billion (ppb) and less than or equal to 1000 parts per million (ppm). In another embodiment, the analyte is present in the sample at a concentration greater than or equal to 1 part per ppb and less than or equal to 100 ppm. In another embodiment, the analyte is present in the sample at a concentration greater than or equal to 1 part per ppb and less than or equal to 10 ppm. In another embodiment, the analyte is present in the sample at a concentration greater than or equal to 10 part per ppb and less than or equal to 1000 ppm. In another embodiment, the analyte is present in the sample at a concentration greater than or equal to 100 part per ppb and less than or equal to 1000 ppm. In another embodiment, the analyte is present in the sample at a concentration greater than or equal to 1 part per ppm and less than or equal to 1000 ppm. In another embodiment, the analyte is present in the sample at a concentration between 1 part per ppb and 10 ppm. In another embodiment, the analyte is present in the sample at a concentration between 1 part per ppb and 750 ppb.

Many VOCs emitted by humans have been correlated with certain diseases. Therefore, in certain embodiments, the analyte is a VOC. A variety of VOCs may be detected by the wearable device of the present disclosure. In one embodiment, any VOC known in the art to be associated with a physiological status, a predisposition of a physiological status, a disease or condition, or a predisposition to a disease or condition may be detected. In one embodiment, a VOC is any carbon based compound with a vapor pressure greater than 0.01 kPa at 293.15 K (20° C.).

In one embodiment, the analyte is a VOC and the VOC is present in the sample at a concentration greater than or equal to 1 part per billion (ppb) and less than or equal to 1000 parts per million (ppm). In another embodiment, the analyte is a VOC and the VOC is present in the sample at a concentration greater than or equal to 1 part per ppb and less than or equal to 100 ppm. In another embodiment, the analyte is a VOC and the VOC is present in the sample at a concentration greater than or equal to 1 part per ppb and less than or equal to 10 ppm. In another embodiment, the analyte is a VOC and the VOC is present in the sample at a concentration greater than or equal to 10 part per ppb and less than or equal to 1000 ppm. In another embodiment, the analyte is a VOC and the VOC is present in the sample at a concentration greater than or equal to 100 part per ppb and less than or equal to 1000 ppm. In another embodiment, the analyte is a VOC and the VOC is present in the sample at a concentration greater than or equal to 1 part per ppm and less than or equal to 1000 ppm. In another embodiment, the analyte is a VOC and the VOC is present in the sample at a concentration between 1 part per ppb and 10 ppm. In another embodiment, the analyte is a VOC and the VOC is present in the sample at a concentration between 1 part per ppb and 750 ppb.

In certain embodiments, a single VOC is detected by the sensor system of the wearable device of the present disclosure. In certain embodiments, more than a single VOC is detected by the sensor system of the wearable device of the present disclosure. In one embodiment, the VOC detected is acetone, methyl nitrate, pentyl nitrate (for example, 2-pentyl nitrate), ethanol, methanol, propanol, methane, propane, ethyl benzene, isoprene, O-xylene (ortho-xylene), M/P-xylene (meta- or para-xylene), formaldehyde, acetaldehyde, or any combination of the foregoing. In another embodiment, the VOC detected is acetone, methyl nitrate, pentyl nitrate (for example, 2-pentyl nitrate), ethanol, methanol, propanol, methane, propane, ethyl benzene, isoprene or any combination of the foregoing.

In another embodiment, the detected VOC is acetone and methyl nitrate, pentyl nitrate (for example, 2-pentyl nitrate), ethanol, methanol, propanol, methane, propane, ethyl benzene, isoprene, O-xylene, M/P-xylene, formaldehyde, acetaldehyde, or any combination of the foregoing. In another embodiment, the detected VOC is acetone and methyl nitrate, pentyl nitrate (for example, 2-pentyl nitrate), ethanol, methanol, propanol, methane, propane, ethyl benzene, isoprene, or any combination of the foregoing. In another embodiment, the detected VOC is acetone and pentyl nitrate (for example, 2-pentyl nitrate), methanol, propane, isoprene, or any combination of the foregoing. In another embodiment, the detected VOC is one or more of acetone, pentyl nitrate (for example, 2-pentyl nitrate), methanol, propane, or isoprene. In another embodiment, the detected VOC is each of acetone, pentyl nitrate (for example, 2-pentyl nitrate), methanol, propane, or isoprene.

In another embodiment, the detected VOC is ethanol and methyl nitrate, pentyl nitrate (for example, 2-pentyl nitrate), acetone, methanol, propanol, methane, propane, ethyl benzene, isoprene, O-xylene, M/P-xylene, formaldehyde, acetaldehyde, or any combination of the foregoing. In another embodiment, the detected VOC is ethanol and methyl nitrate, pentyl nitrate (for example, 2-pentyl nitrate), ethanol, acetone, propanol, methane, propane, ethyl benzene, isoprene, or any combination of the foregoing. In another embodiment, the detected VOC is ethanol and one or more of methyl nitrate or ethyl benzene. In another embodiment, the detected VOC is each of ethanol, methyl nitrate and ethyl benzene.

In another embodiment, the detected VOC is isoprene and acetone, methyl nitrate, pentyl nitrate (for example, 2-pentyl nitrate), ethanol, methanol, propanol, methane, propane, ethyl benzene, O-xylene, M/P-xylene, formaldehyde, acetaldehyde, or any combination of the foregoing.

In certain embodiments, the VOC detected is acetone and optionally 1 or more additional VOCs. In certain embodiments, the VOC detected is isoprene and optionally 1 or more additional VOCs. In certain embodiments, the VOC detected is methyl nitrate and optionally 1 or more additional VOCs. In certain embodiments, the VOC detected is pentyl nitrate (for example, 2-pentyl nitrate) and optionally 1 or more additional VOCs. In certain embodiments, the VOC detected is ethanol and optionally 1 or more additional VOCs. In certain embodiments, the VOC detected is methanol and optionally 1 or more additional VOCs. In certain embodiments, the VOC detected is propanol and optionally 1 or more additional VOCs. In certain embodiments, the VOC detected is methane and optionally 1 or more additional VOCs. In certain embodiments, the VOC detected is propane and optionally 1 or more additional VOCs. In certain embodiments, the VOC detected is ethyl benzene and optionally 1 or more additional VOCs. In certain embodiments, the VOC detected is O-xylene and optionally 1 or more additional VOCs. In certain embodiments, the VOC detected is M/P-xylene and optionally 1 or more additional VOCs. In certain embodiments, the VOC detected is formaldehyde and optionally 1 or more additional VOCs. In certain embodiments, the VOC detected is acetaldehyde and optionally 1 or more additional VOCs.

When more than one VOC is detected by the sensor system, at least 2 VOCs may be detected, at least 3 VOCs may be detected, at least 4 VOC may be detected, at least 5 VOCs may be detected, at least 6 VOCs may be detected, at least 7 VOCs may be detected, at least 8 VOCs may be detected, at least 9 VOCs may be detected, or more than 9 VOCs may be detected. In the foregoing, the upper range for the number of VOCs detected may be 15, 20, 25 or 50 VOCs. Therefore, as one example, when at least 2 VOCs are detected, from 2 to 15 VOCs, from 2 to 10 VOCs, from 2 to 5 VOCs, from 2 to 4 VOCs, or from 2 to 3 VOCs may be detected by the sensor system.

In one embodiment, the VOCs and combinations are as disclosed in Siegal, et al. (J. Breath Res, 11(2), 2017), which is hereby incorporated herein by reference for such teachings. In one embodiment, the VOCs and combinations are as disclosed in Greiter, et al. (Diabetes Technol Ther, 12, pp 455-463, 2010), which is hereby incorporated herein by reference for such teachings.

While the present disclosure provides for the detection of VOCs regardless of the reason why such VOC is associated with a particular physiological status, scientific principles may inform what VOCs may be associated with a particular physiological status. Human breath is composed of inhaled air, $CO_2$, water vapor, small amounts of proteins, and VOCs. The VOCs are created through a variety of physiological process and non-physiological processes, including, but not limited to, internal metabolic reactions, metabolic reactions from bacteria or other organisms present in the body, as gases produced for physiological signaling roles, or as metabolites from inhaled atmospheric components.

By way of example only, the following provides a scientific basis for the utility of selected VOCs in the determination of a hypoglycemia.

Acetone may be derived from decarboxylation of acetoacetate, which is produced from lipolysis or lipid peroxidation. The synthesis and degradation of such ketone bodies is therefore related to blood glucose levels.

Pentyl nitrate (for example, 2-pentyl nitrate) and methyl nitrate may be generated through pathways involving organic peroxy radical ($RO_2\cdot$), superoxide ion ($O_2\cdot^-$), or other byproducts of oxidative reactions. As oxidative stress is associated with hypoglycemia, levels of these compounds may reflect changes in oxidative status indicative of hypoglycemia.

Ethanol, methanol, propanol, and propane production may be due activity of gut flora bacteria (for example, alcoholic fermentation of glucose by gut bacteria and yeast). As such, the levels of ethanol and methanol are responsive to fluctuations in glucose concentration.

Ethyl benzene, O-xylene, and M/P-xylene are generally inhaled, partly metabolized by liver, and then exhaled at lower concentration. Rapid-onset hyperglycemia may suppress hepatic metabolism causing increased concentration of these compounds in exhaled air.

In one embodiment, the physiological status is hypoglycemia and the VOC is acetone, methyl nitrate, pentyl nitrate (for example, 2-pentyl nitrate), ethanol, methanol, propanol, methane, propane, ethyl benzene, isoprene, O-xylene, M/P-xylene, formaldehyde, acetaldehyde or combinations of the foregoing.

In certain embodiments, the physiological status is hypoglycemia and the VOC detected is: (1) acetone, methyl nitrate, pentyl nitrate (for example, 2-pentyl nitrate), ethanol, methanol, propanol, methane, propane, ethyl benzene, isoprene, O-xylene; M/P-xylene, formaldehyde, acetaldehyde, or any combination of the foregoing; (2) acetone, methyl nitrate, pentyl nitrate (for example, 2-pentyl nitrate), ethanol, methanol, propanol, methane, propane, ethyl benzene, isoprene or any combination of the foregoing; (3) acetone and methyl nitrate, pentyl nitrate (for example, 2-pentyl nitrate), ethanol, methanol, propanol, methane, propane, ethyl benzene, isoprene, O-xylene, M/P-xylene, formaldehyde, acetaldehyde, or any combination of the foregoing; (4) acetone and methyl nitrate, pentyl nitrate (for example, 2-pentyl nitrate), ethanol, methanol, propanol, methane, propane, ethyl benzene, isoprene, or any combination of the foregoing; (5) acetone and pentyl nitrate (for example, 2-pentyl nitrate), methanol, propane, isoprene, or any combination of the foregoing; (6) ethanol and methyl nitrate, pentyl nitrate (for example, 2-pentyl nitrate), acetone, methanol, propanol, methane, propane, ethyl benzene, isoprene, O-xylene, M/P-xylene, formaldehyde, acetaldehyde, or any combination of the foregoing; (7) ethanol and methyl nitrate, pentyl nitrate (for example, 2-pentyl nitrate), ethanol, acetone, propanol, methane, propane, ethyl benzene, isoprene, or any combination of the foregoing; (8) ethanol and methyl nitrate, ethyl benzene, or any combination of the foregoing; (9) isoprene and acetone, methyl nitrate, pentyl nitrate (for example, 2-pentyl nitrate), ethanol, methanol, propanol, methane, propane, ethyl benzene, O-xylene, M/P-xylene, formaldehyde, acetaldehyde, or any combination of the foregoing; 10) ethanol, methyl nitrate, and ethyl benzene; or 11) acetone, pentyl nitrate (for example, 2-pentyl nitrate), methanol, propane, and isoprene.

In certain embodiments, the physiological status is hypoglycemia and the VOC detected is acetone and optionally 1 or more additional VOCs. In certain embodiments, the physiological status is hypoglycemia and the VOC detected is isoprene and optionally 1 or more additional VOCs. In certain embodiments, the physiological status is hypoglycemia and the VOC detected is methyl nitrate and optionally 1 or more additional VOCs. In certain embodiments, the physiological status is hypoglycemia and the VOC detected is pentyl nitrate (for example, 2-pentyl nitrate) and optionally 1 or more additional VOCs. In certain embodiments, the physiological status is hypoglycemia and the VOC detected is ethanol and optionally 1 or more additional VOCs. In certain embodiments, the physiological status is hypoglycemia and the VOC detected is methanol and optionally 1 or more additional VOCs. In certain embodiments, the physiological status is hypoglycemia and the VOC detected is propanol and optionally 1 or more additional VOCs. In certain embodiments, the physiological status is hypoglycemia and the VOC detected is methane and optionally 1 or more additional VOCs. In certain embodiments, the physiological status is hypoglycemia and the VOC detected is propane and optionally 1 or more additional VOCs. In certain embodiments, the physiological status is hypoglycemia and the VOC detected is ethyl benzene and optionally 1 or more additional VOCs. In certain embodiments, the physiological status is hypoglycemia and the VOC detected is O-xylene and optionally 1 or more additional VOCs. In certain embodiments, the physiological status is hypoglycemia and the VOC detected is M/P-xylene and optionally 1 or more additional VOCs. In certain embodiments, the physiological status is hypoglycemia and the VOC detected is formaldehyde and optionally 1 or more additional VOCs. In certain embodiments, the physiological status is hypoglycemia and the VOC detected is acetaldehyde and optionally 1 or more additional VOCs.

Sensor System

A variety of sensors may be used in the devices of the present disclosure. In one embodiment, any sensor known in the art to detect an analyte of interest may be used. In one embodiment, any sensor known in the art to detect a VOC of interest may be used. In another embodiment, the sensor is a semi-conductor metal oxide sensor, an electrochemical sensor, a field effect transistor sensors, resistive sensors, a chemiresistive sensor, or capacitive sensors. In one embodiment, a property of each of the foregoing sensors is altered upon interaction with an analyte.

In certain embodiments, the sensor may be modified to show increased sensitivity and/or selectivity by modifying the sensor to increase or decrease adsorption and/or transduction efficiency for specific a specific analyte, including a VOC.

The sensor comprises a sensor material capable of detecting the analyte (for example, a VOC). The analyte, on interacting with/binding to the sensor material cause a change in a physical property, a chemical property, and/or an electronic property of the material resulting in a signal. In one embodiment, the signal is directly correlated to the presence, amount, or concentration of the analyte in the sample. In one embodiment, the signal is a change in an electrical property, such as, but not limited to, a change in conductivity (resistance), a change in capacitance, or a change in current of the sensor material or the sensor containing the sensor material. The signal is analyzed by the controller to produce a result for a given analyte.

In one embodiment, a nanomaterial is coated with the sensor material. The nanomaterials may be formed of a variety of materials. In one embodiment, the nanomaterials are selected from the group consisting of gold nanoparticles, carbon nanotubes, graphene, fullerene, carbon black, and combinations thereof. The nanomaterials are coated with a surface coating of the sensor material. In one embodiment, the sensor material comprises one or more functional groups selected from the group consisting of $C_1$-$C_{20}$ thiol-alkanes, $C_1$-$C_{20}$ thiol-aromatics, polycyclic aromatic hydrocarbons, carboxylic acid, decanethiol, dodecanethiol, tert-dodecanethiol, 4-methoxy-toluenethiol, 2-nitro-4-trifluoro-methylbenzenethiol, 2-mercaptobenzoxazole and combinations thereof. In another embodiment, the sensor material is polypyrrole, low-density polyethylene (LDPE), poly(ethylene-block-ethylene oxide) (PE-b-PEO), polyethylene glycol (PEG), polymethylmethacrylate (PMMA), poly(vinylidene fluoride-hexafluoropropylene) (PVDF-HFP), or combinations thereof. In another embodiment, the sensor material is $TiO_2$, $SnO_2$, $Cr_2O_3$, $Mn_2O_3$, $Co_3O_4$, NiO, CuO, SrO, $In_2O_3$, $WO_3$, $V_2O_3$, $Fe_2O_3$, $GeO_2$, $Nb_2O_5$, $MoO_3$, $Ta_2O_5$, $La_2O_3$, $CeO_2$, $Nd_2O_3$, either with or without suitable dopants (such as, but not limited to, tungsten, palladium, platinum, titanium, lanthanum, and zinc)

In certain embodiments, the sensor system comprises a plurality of sensors, with a subset of the plurality of sensors designed to detect a specific analyte (for example, a specific VOC) such that a number of distinct analytes may be detected by the sensor system.

In one embodiment, the sensor is one as described in Kim et al. (Exhaled Breath Sensors, in Smart Sensors for Health and Environment Monitoring, C.-M Kyung (ed), Springer Science+Business Media, 2015), which is hereby incorporated herein by reference for such teachings.

In preferred embodiments, the sensor system comprises at least one sensor as described herein and a data module in communication with the sensor for storing the signal generated by the sensor. When more than one sensor is present, a data module is present for each sensor of the sensor system. The sensor and the data module may be a single element of multiple elements. The data module may transmit the signal to the controller or a separate computing device (such as a smartphone, tablet, laptop or computer) and the signal is stored and/or processed by the controller of the device or a processor of the separate computing device.

Alternatively, each sensor of the sensor system transmits the signal directly to the controller of the device or to a processor of the separate computing device (such as a smartphone, tablet, laptop or computer) and the signal is stored and/or processed by the separate computing device.

In one embodiment, a sensor as described in the present application is a metal oxide sensor. Resistance of the metal oxide sensing layer is altered when target analytes are present. In operation, oxidizing gases such as nitrogen dioxide and ozone cause resistance to increase, while reducing gases like VOCs and carbon monoxide cause the resistance to go down. Regulating the heater power and/or doping the metal oxide layer can be used to adjust the selectivity of the sensors. For VOC detection, metal oxide sensors that show the highest sensitivity to reducing gasses are preferred. This typically means sensors with tin oxide, with and without dopants such as, but not limited to, tungsten, palladium, platinum, titanium, lanthanum, zinc and other dopants, heated to temperatures between 300-700 degrees C. other oxides that may be used include, but are not limited to, $TiO_2$, $Cr_2O_3$, $Mn_2O_3$, $Co_3O4$, NiO, CuO, SrO, $In_2O_3$, $WO_3$, $V_2O_3$, $Fe_2O_3$, $GeO_2$, $Nb_2O_5$, $MoO_3$, $Ta_2O_5$, $La_2O_3$, $CeO_2$, and $Nd_2O_3$, either with or without suitable dopants. Alternately, metal oxide sensors that have different dopants can be used. For example, a tin oxide sensor and a tungsten-doped tin oxide sensor with or without different heater temperatures, can be used to vary selectivity to a subset of analytes.

In one embodiment, a sensor as described in the present disclosure is a chemiresistive sensor. Such sensor may be created by depositing a nano-nucleated or nano-structured material onto a prefabricated electrode (preferably a microelectrode). The nano-nucleated material provides a specificity to the sensor to detect a single analyte (for example, acetone) or a group of related analytes (for example, O-xylene and M/P-xylene). The sensor interacts with gaseous analytes (i.e., chemical compounds) in the sample altering one or more electrical properties of the sensor (for example, a change in resistance). The change in electrical properties is used to determine the presence, amount or concentration of the analyte in the sample. In a particular embodiment, a sensor system is comprised of a support containing a plurality of channels, wherein each channel contains a sensor (an electrode at least partially coated with nano-nucleated material).

In one embodiment, the sensor or sensor system is as described in U.S. patent application Ser. No. 16/548,801, which is hereby incorporated by reference for such teachings. In one embodiment, the sensor or sensor system is as described in U.S. patent application Ser. No. 16/547,499, which is hereby incorporated by reference for such teachings.

In one embodiment, the signal (the change in electrical properties) from a sensor is combined with digital signal processing to detect analytes of interest found in human breath. In one embodiment, the signal from a sensor is optionally subject to a signal conditioning step (such as, but not limited to, noise filtering, amplification and the like). The signal from each sensor (regardless of whether the signal is subject to a preconditioning step) is then analyzed to determine the presence, amount, or concentration of the analyte in the sample. In one embodiment, the signal is subject to a pattern recognition technique to separate the signal from an analyte of interest from nuisance signals such as humidity, temperature, and cross-sensitive gases. This sensor configuration provides for detecting VOCs in human breath in the parts-per-billion (ppb) range at ambient temperature.

In one embodiment, the signal is processed as described in U.S. patent application Ser. No. 16/548,763, which is hereby incorporated by reference for such teachings. In one embodiment, the signal is processed as described in U.S. patent application Ser. No. 16/547,499, which is hereby incorporated by reference for such teachings. In one embodiment, the signal is processed as described in U.S. Patent Application No. 62/799,537, which is hereby incorporated by reference for such teachings.

Controller

In one embodiment, the controller is programmed to perform at least one of the following: i) initiate a sampling process; ii) receive the output of the sensor system (i.e., a signal generated by the sensor system); iii) evaluate the output of the sensor system to determine the presence, amount, and/or concentration of the analyte in the sample from the user (i.e., a result); iv) determine if the presence, amount, and/or concentration of the analyte is within an acceptable range for a physiological status or outside of an acceptable range for a physiological status; v) alert the user to the result; vi) alert the user if the test result is within an acceptable range or outside of an acceptable range; vii) store any of the foregoing in a memory; viii) transmit the signal to a separate computing device (which may then accomplish any one of steps iii) to vii) in any combination); or ix) any combination of the foregoing.

As used herein, the controller of the device is equivalent to a processor as described herein.

In one aspect of this embodiment, the step "initiate the sampling process" comprises at least one of the following: i) activating the sensor system to detect the analyte; ii) determining a sampling parameter; iii) evaluating the sampling parameter to determine if the sampling process can be completed; and iv) modifying a device parameter to facilitate the sampling process.

In another aspect of this embodiment, the step "initiate the sampling process" comprises at least one of the following: i) determining a sampling parameter; ii) evaluating the sampling parameter to determine if the sampling process can be completed; iii) optionally modifying a device parameter to facilitate the sampling process; iv) activating the sensor system to detect the analyte if the sampling process can be completed. If the sampling process cannot be completed, the user may be alerted that the sampling process cannot be completed and optionally provided the reason why the sampling process cannot be completed (based on the sampling parameter).

For example, certain sampling parameters (as discussed herein) may be known to interfere with proper detection of the analyte (for example, a high concentration of $CO_2$ or a relative humidity over 60%). In this case, a user could, for example, move to another location that had a decreased $CO_2$ concentration or less relative humidity. Alternatively, the user could bring the device close to the mouth an exhale into the device. Further, the user could simply skip the monitoring process at that time or use an alternate method to monitor the analyte.

In one aspect of this embodiment, the step "initiate the sampling process" is accomplished without requiring the user to exhale into the wearable device. In another aspect of this embodiment, no action of the user is required to initiate the sampling process. In another aspect of this embodiment, no action of the user is required for any action after the sampling process is initiated in order to provide a result. As such, the present disclosure provides for a wearable device that automates the monitoring process.

Neural networks, cluster analysis, and other artificial intelligence systems may be coupled with the wearable device of the present disclosure. The foregoing may serve to train the sensor system, train the controller (for example, determining when to initiate a reading or evaluating a sampling parameter), refine what is within an acceptable range for a physiological status or outside of an acceptable range for a physiological status, and/or to provide further analysis of a result (i.e., the presence, amount or concentration of an analyte). Furthermore, the foregoing may be used to refine a result over time and customize a result to each particular user over time. The neural networks, cluster analysis, and other artificial intelligence systems may be incorporated as a part of the controller, may be present as a separate component of the wearable device, or may be present as a program on a receiving device.

In a specific embodiment, multiple neural network modules with back propagation algorithms are used for pattern recognition following processing of the data (such as by the controller). The back propagation algorithm is based on gradient descent in an error method which minimizes the mean square error between the network's output and the desired output for all input patterns. Back-propagation is a multi-layer feedforward network which has one input, one output, and at least one hidden layer. Each layer is fully connected to the succeeding layer. During the learning process, the input vectors and the output of each neuron are computed layer by layer. The differences between the outputs of the final layer and the desired target vectors are back-propagated to the previous layer(s), modified by the derivative of the transfer function, and the connection weights are adjusted using the Widrow-Hofflearning rule.

Using this process, an intelligent classifier with multi-module neural network is constructed with each one dedicated to specific vapor group to perform vapor recognition. Each module consists of a back propagation algorithm network with its own suitable architecture. The use of a multi-module neural network eliminates the need for housing all the identification knowledge for all target VOCs in a single network. By using multiple networks, each network is trained for a specific VOC.

General Description of the Wearable Device

The wearable device may be worn by the user such that the wearable device is positioned as desired. In one embodiment, the wearable device is worn on the wrist. In another embodiment, the wearable device is worn around the neck. In other embodiment, the wearable device is reversible attached to an article of clothing. In another embodiment, the wearable device is placed adjacent to a particular region of the body, such as, but not limited to, the underarm, chest, or stomach. In another embodiment, the wearable device is placed adjacent to a particular region of the body, such as, but not limited to, the underarm, chest, or stomach and worn underneath an item of clothing (such as, but not limited to, underneath a shirt. The wearable device may further comprise elements to accommodate the wearing and/or placement of the device, such as a wristband, clip, strap, adhesive pad and the like.

In one embodiment, the wearable device 1 comprises the following components: i) a housing 10, ii) an inlet port 20; iii) a chamber 30 in the interior of the housing; iv) an inlet passage 40 having a first end 41 in fluid communication with the inlet port 20 and a second end 42 in fluid communication with the chamber 30; v) a sensor system 50; and vi) a controller 60 in communication with the sensor system.

The housing functions to enclose the various components of the wearable device and protect the components from damage and the environment. The housing may be of any shape desired and the shape s not critical provided the shape allows for the various components and functions described herein. The housing is manufactured from any desired material, such as but not limited to, impact resistant plastics and polymers, metals, or combinations thereof. The housing defines an interior portion, at least a portion of which is hollow to allow the additional components to be contained within the housing. As described herein, the housing may contain one or more openings in the exterior of the housing that are in communication with the hollow interior portion of the device.

The inlet port allows the sample (for example, ambient air) to enter the wearable device and contact the sensor system. The inlet port is in fluid communication with the exterior of the housing and forms an opening in the exterior of the housing.

An inlet channel is in fluid communication with the inlet port at a first end and in fluid communication with an interior portion of the wearable device (such as the chamber) at a second end. The inlet channel serves to deliver the sample (for example, ambient air) to the sensor system. A membrane (as described below) may also be positioned at the inlet port or between the inlet port and the chamber. In certain embodiments, the membrane is present and is positioned at the first or second end of the inlet channel. In certain embodiments, the membrane is present and is positioned at or adjacent to the inlet port.

In certain embodiments, the inlet channel comprises a constriction point. A constriction point defined as a portion of the inlet channel that has a diameter that is less than the diameter of a portion of the inlet channel immediately preceding and/or immediately following the construction point. The constriction point serves to increase the flow rate of the sample as it travels through the inlet channel. The constriction point may be positioned as desired in the inlet channel. In one aspect of this embodiment, the constriction point is positioned at or adjacent to the first or second end of the inlet channel. In another aspect of this embodiment, the constriction point is positioned between the first and second end of the inlet channel. The second end of the inlet channel is preferably positioned to allow the sample to contact the sensor system. In certain embodiments, one or more transfer channels direct the sample directly to the sensor system. The transfer channels when present may have a first end in communication with the second end of the inlet channel and a second end in communication with a portion of the sensor system.

The chamber defines a hollow area in the interior of the housing and functions to provide a space to house the components of the wearable device (for example, the sensor system and/or the controller). The chamber is in fluid communication with the inlet port, via the inlet channel, and the exit port (when present), via the exit channel. The chamber may house a single component or multiple components of the wearable device. The wearable device may contain a single chamber of more than one chamber, with each chamber optionally being in fluid communication with one or more additional chambers.

The sensor system allows for the detection of the analyte in the sample. In certain embodiments, the sample is ambient air and the analyte is one or more VOCs. The sensor system is described in more detail herein and any sensor system described herein may be used in the wearable devices described. In certain embodiments, the sensor system is located in the chamber.

In certain embodiments, the sensor system and the controller are placed on a printed circuit board and interconnected as is known in the art.

In another embodiment, the wearable device 1 comprises i) a housing 10, ii) a plurality of inlet ports 20; iii) a chamber 30 in the interior of the housing; iv) an inlet passage 40 for each inlet port 20, each inlet passage having a first end 41 in fluid communication with its inlet port 20 and a second end 42 in fluid communication with the chamber 30; v) a sensor system 50; and vi) a controller 60 in communication with the sensor system.

In one aspect of this embodiment, the wearable device comprises a first and a second inlet port and a first and a second inlet channel. The first and second inlet ports may be positioned in a desired geometric relationship to each other. The geometric relationship may be selected to provide efficient introduction of the sample to the sensor system and/or to allow a sample to be obtained from different areas surrounding the wearable device. In one aspect of this embodiment, the first and second inlet ports are positioned on opposite sides of the housing. In one aspect of this embodiment, the first and second inlet ports are positioned substantially in line with one another. By substantially in line with one another, it is meant that when a straight line is drawn through the center of one inlet port (for example, the first inlet port), the center of the other inlet port (for example, the second inlet port) will be within 5 degrees in any direction of said line.

In one aspect of this embodiment, the wearable device comprises a first, a second, a third, and a fourth inlet port and a first, a second, a third, and a fourth inlet channel. The first, second, third, and fourth inlet ports may be positioned in a desired geometric relationship to each other. The geometric relationship may be selected to provide efficient introduction of the sample to the sensor system and/or to allow a sample to be obtained from different areas surrounding the wearable device. In one aspect of this embodiment, the first and second inlet ports are positioned substantially in line with one another and the third and fourth inlet ports are positioned substantially in line with one another.

In certain embodiments, the sensor system and the controller are placed on a printed circuit board and interconnected as is known in the art.

The wearable device in any of the embodiments described may optionally include additional components as described below.

In one embodiment, the wearable device further comprises a wireless communication module. The wireless communications module can include one or more types of wireless communications devices, including, for example, a radio frequency, Bluetooth, or global system for mobile communication system transmission devices. In certain embodiments, the wireless communication occurs via a direct WiFi connection (802.111 b/g/n) or e cell connection, such as a 4G or 5G cell connection. The wireless module is in communication with the controller to allow for transmission of information to a receiving device (such as, but not limited to, a mobile phone, tablet, cell phone, computer, or other type of personal computing device). In certain aspects of this embodiment, the communication between the wearable device and the receiving device is encrypted to ensure privacy. Suitable encryption methods include, but are not limited to, PGP, GnuPG, GPG4Win, Axcrypt and others. When the communication is encrypted, a key can be selected when the wearable device is first used which can be programmed into the receiving device. The appropriate key is transmitted by the wearable device along with the data. In certain embodiments, when the wireless communication module is present, the sensor system, the controller and the wireless communication module are placed on a printed circuit board and interconnected as is known in the art.

In one embodiment, the wearable device further comprises a membrane. The function of the membrane is to prevent or reduce the amount of particulates suspended in the sample of ambient air from entering chamber while allowing the analyte to pass through freely with the sample of ambient air. In addition, in certain embodiments the membrane is made of a material that removes or reduces the amount of moisture in the sample of ambient air. Moisture can interfere with the operation of certain sensors described herein. Suitable materials include, but are not limited to, low density polyethylene, high density polyethylene, polypropylene, oriented polypropylene. In certain embodiments, the membrane is positioned at the inlet port or between the inlet port and the chamber.

In one embodiment, the wearable device further comprises an exit port. The function of the exit port is to allow the sample (for example, ambient) air to exit the wearable device after coming into contact with the sensor system. The exit port is in fluid communication with the exterior of the housing and forms an opening in the exterior of the housing. An exit channel is in fluid communication with the exit port at a first end and in fluid communication with an interior portion of the wearable device at a second end (such as the chamber). A membrane (as described above for the inlet channel) may also be positioned at the exit port or between the exit port and the chamber.

In one embodiment, the wearable device further comprises a pump assembly. The pump assembly functions to assist in drawing a sample (such as ambient air) through the inlet port to the chamber where the sample contacts the sensor system. The pump assembly may also aid in removing the sample from the sample chamber if desired. The pump assembly may be an electric fan, a micropump, or a peristaltic pump. The pump assembly may be located in the interior portion of the housing suitable for drawing a sample into the device. For example, in certain aspects the pump assembly is located at the second end of the exit channel or adjacent to and in fluid communication with the second end of the exit channel. The pump assembly may also be located at the second end of the inlet channel or adjacent to and in fluid communication with the second end of the inlet channel. Other positions are also within the scope of the present disclosure.

In one embodiment, the wearable device further comprises a closure of the inlet port/inlet channel and/or the exit port/exit channel. When present such a closure may be in communication with the controller and opened when a sample is taken and closed during other times. Suitable closures and their operation are known in the art.

In one embodiment, the wearable device further comprises a user input. The user input may be used when the user desires to initiate a reading other than one that is programmed by the controller. The user input is in communication with at least the controller and may be in the form of a push button or the like.

In one embodiment, the wearable device further comprises a notification module. The notification module on the wearable device serves to alert the user to a result. The notification module is in communication with at least the controller. The notification module may be a visual display (such as, for example, an LED display), an audible function (such as, for example a chirp, beep or tone), or a tactile function (such as, for example, a vibration). In certain embodiments, the notification module is a visual display and may take the form of one or more circular LEDS that displays a green light when the result is within an acceptable range, that displays a red light when the result is outside of an acceptable range, or that displays a yellow light when the result approaches (for example, is within 10% of) being outside of an acceptable range.

In certain preferred embodiments, the wearable device in any of the embodiments described further comprises the wireless communication module.

In certain preferred embodiments, the wearable device in any of the embodiments described further comprises the exit port and the pump assembly.

In certain preferred embodiments, the wearable device in any of the embodiments described further comprises the membrane.

In certain preferred embodiments, the wearable device in any of the embodiments described further comprises the wireless communication module, the exit port, and the pump assembly.

In certain preferred embodiments, the wearable device in any of the embodiments described further comprises the wireless communication module and the membrane.

In certain preferred embodiments, the wearable device in any of the embodiments described further comprises the wireless communication module, the exit port, the pump assembly, and the membrane.

FIG. 1 shows a perspective view of one embodiment of the wearable device 1 of the present disclosure. The wearable device 1 is illustrated further comprising a band 200 (such as, for example, a watch band) allowing the user to place the wearable device 1 on the wrist. The housing 10, inlet port 20, membrane 25 (shown with hatch marks), user input 100, and notification module 102 are also illustrated.

Figure 2:
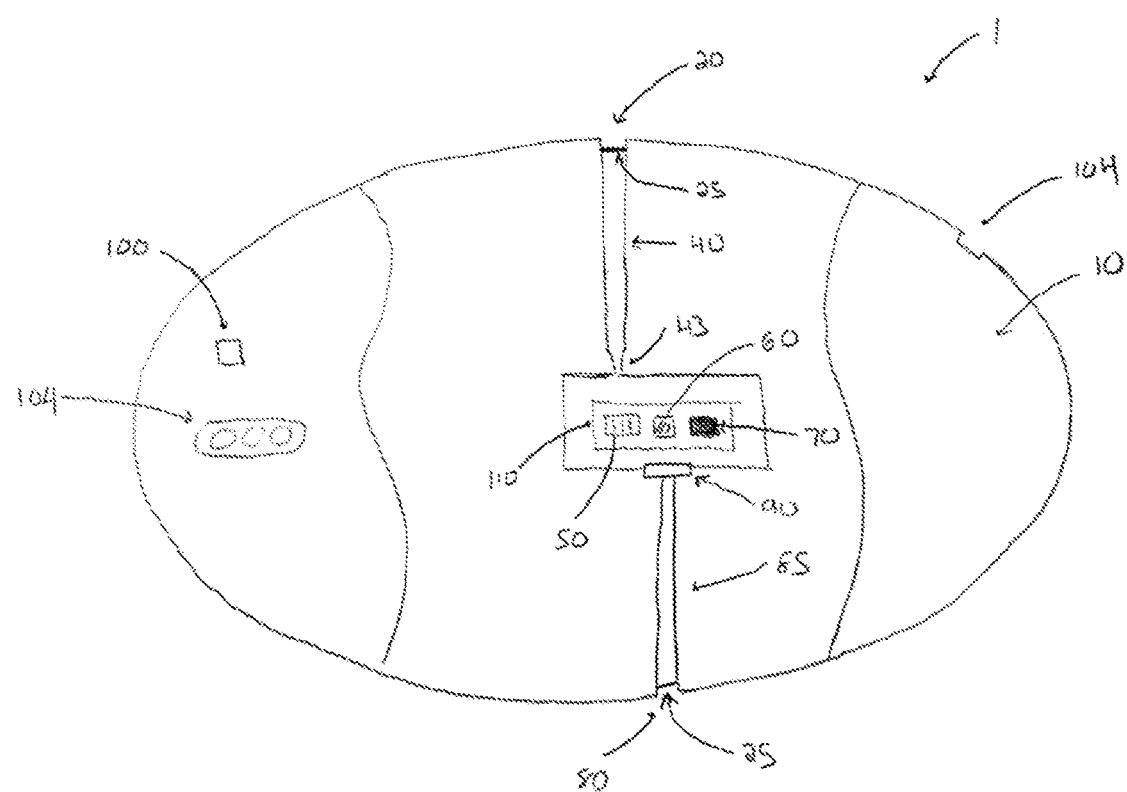
FIG. 2 shows an exemplary configuration of the wearable device of the present disclosure.

FIG. 2 shows a partially exploded view of an exemplary embodiment of the wearable device 1. The wearable device is shown comprising a single inlet port 20, a single inlet passage 40 with a constriction point 43, a chamber 30, a sensor system 50, a controller 60, a wireless module 70, an exit port 80, an exit channel 85, a pump assembly 90, and a membrane 25 positioned at the inlet port 20 and the exit port 80. The device further comprises a user input 100, a notification module 102 in the form of a series of LED lights, and an input port 104 for connecting to a separate computing device (i.e., a receiving device). In FIG. 2 the pump assembly 90 is located opposite the inlet port 20, although other locations for pump assembly 90 are within the scope of the present disclosure.

Figure 3:
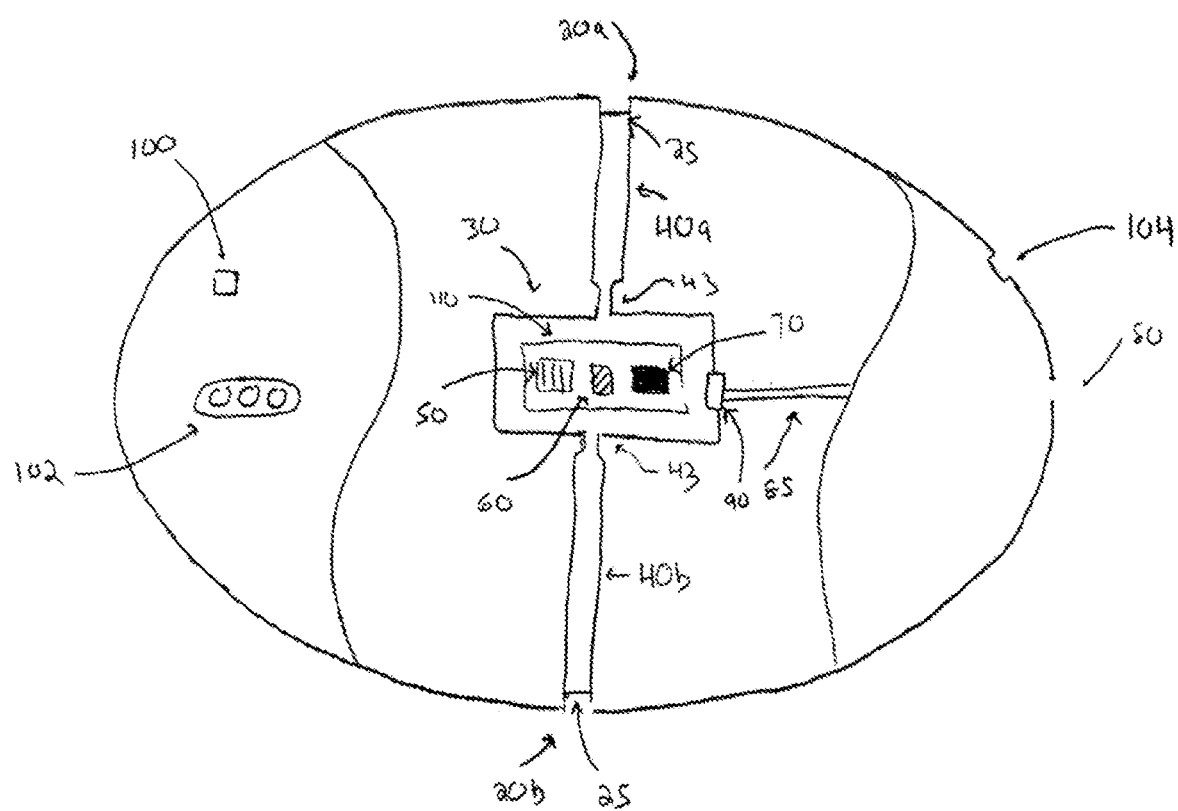
FIG. 3 shows an alternative exemplary configuration of the wearable device of the present disclosure.

FIG. 3 shows an exemplary embodiment of the wearable device 1 comprising two inlet ports 20a and 20b, two inlet passages 40a and 40b with each inlet passage comprising a constriction point 43, a chamber 30, a sensor system 50, a controller 60, a wireless module 70, an exit port 80, an exit channel 85, a pump assembly 90, and a membrane 25 positioned at the inlet ports 20a and 20b and the exit port 80. In this embodiment, the sensor system 50, controller 60, and wireless module 70 are present on a printed circuit board 110. The device further comprises a user input 100, a notification module 102 in the form of a series of LED lights, an input port 104 for connecting to a separate computing device (i.e., a receiving device).

Figure 4:
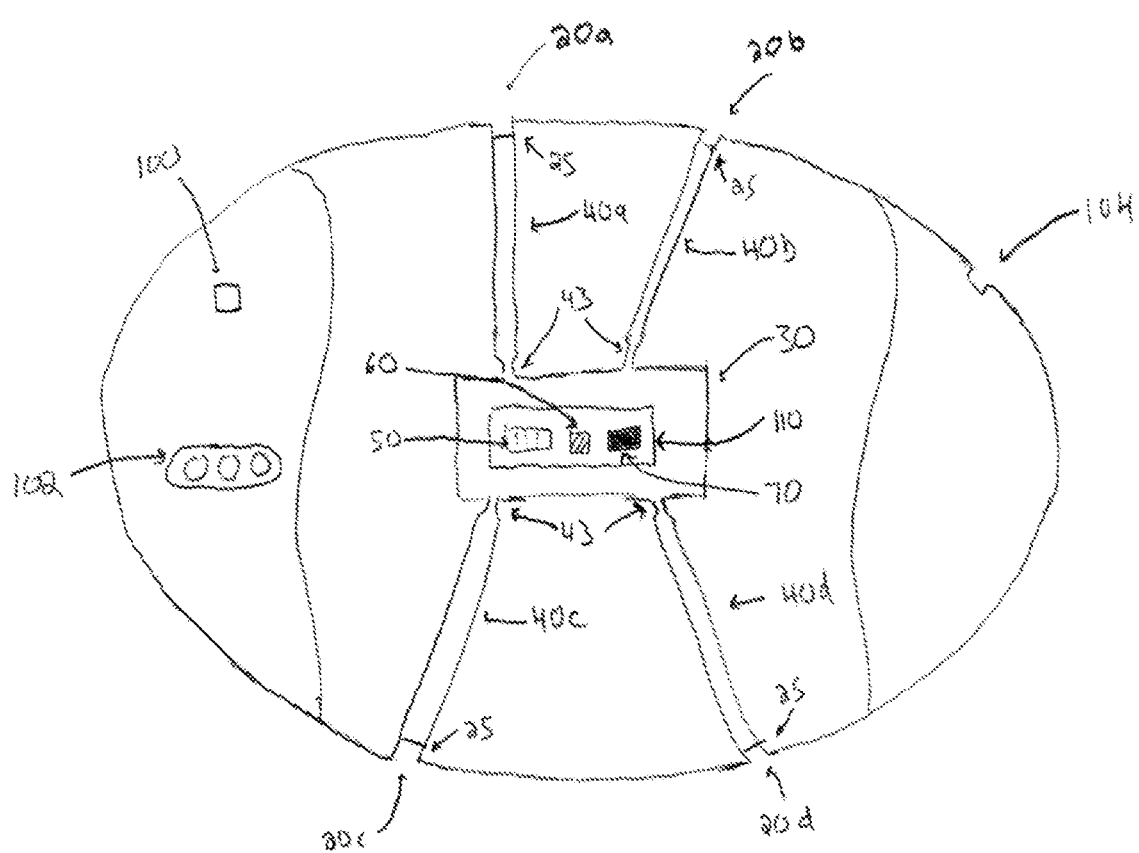
FIG. 4 shows an alternative exemplary configuration of the wearable device of the present disclosure.

FIG. 4 shows an exemplary embodiment of the wearable device 1 comprising four inlet ports 20a to 20d, four inlet passages 40a to 40d with each inlet passage comprising a constriction point 43, a chamber 30, a sensor system 50, a controller 60, a wireless module 70, an exit port 80, an exit channel 85, a pump assembly 90, and a membrane 25 positioned at the inlet ports 20a to 20d and the exit port 80. In this embodiment, the sensor system 50, controller 60, and wireless module 70 are present on a printed circuit board 110. The device further comprises a user input 100, a notification module 102 in the form of a series of LED lights, and a port for connecting to a receiving device or other computing device. In FIG. 4 the pump assembly 90, exit port 80, and exit channel 85 are located beneath the printed circuit board 90 (not shown), although other locations for pump assembly 90 are within the scope of the present disclosure.

Establishment of Baseline Value, Training, and Evaluation of Sampling Parameters In one embodiment, the wearable devices, systems and/or methods of the present disclosure provide for the establishment of a baseline (also referred to herein as a "baseline value") for a specific user. The baseline value reflects a result determined in the absence of an analyte. The baseline value may be stored by the controller and the baseline value may be subtracted from any value determined as described herein.

The wearable device may also be trained to adjust a result to a particular user. In one embodiment, a result is provided by the wearable device. The result is stored by the device and/or a separate computing device. The user then tests for the physiological status by an independent means (for example, when hypoglycemia is the physiological status, by measuring blood glucose levels by a finger prick test or other prior art test). The blood glucose level determined is provided (for example, through an application of the receiving device or an input on the wearable device). The independently determined result may be noted to be within an acceptable range for the physiological status or outside an acceptable range for the physiological status. The independently determined result is then matched to the result obtained with the wearable device (for example, if the result obtained with the wearable device is a concentration of six VOCs and the independently determined result is blood glucose concentration, the concentration of the six VOCs is matched to the corresponding glucose concentration). The training process may be repeated any number of times. In certain embodiments, the training process is carried out when the wearable device is initially worn by the user. In certain embodiments, the training process is carried out after the wearable device has been worn by the user for a period of time. The neural networks, cluster analysis, and/or other artificial intelligence systems may also be used in the training process (for example, to extrapolate additional training results from the received training process). When the training process is carried out multiple times, a specific VOC or a specific combination of VOCs may be identified that correlate with the greatest accuracy and repeatability with the independently determined results. As such, through the training process, the nature of the VOCs detected for each individual may be refined over time for each user. The neural networks, cluster analysis, and/or other artificial intelligence systems may also be used in this analysis.

In addition, parameters of operation of the wearable device may be determined for the user under specific conditions or based on certain parameters associated with the tests. As such, it may be determined that certain parameters adversely impact the accuracy of a result and when such a parameter is determined to be present, the presence of the parameter may be noted in a result or the value may be discarded. In certain aspects of this embodiment, the controller determines and records a sampling parameter associated with a result. Such a sampling parameter includes, but is not limited to, i) the presence of an environmental factor; ii) a temporal factor (for example, the time at which the sampling process is initiated, terminated, and/or completed); iii) a dietary factor (for example, the time at which the user last consumed a food or beverage item or the consumption of a specific food or beverage item); and iv) a physiologic factor (for example, the time at which a specific activity undertaken by the user, the general well-being of the user); and v) a medication factor (for example, any prescription medications or non-prescription items the user may be taking). The various sampling parameters may be input by the user, such as through a receiving device, and then transmitted to the controller of the wearable device, or may be obtained from a third party (for example, for environmental conditions, or may be obtained by an additional sensor on the wearable device).

The controller may tag a result with one or more of the sampling parameters. When a result obtained with the wearable device do not correlate with a result determined at the same general time by another method, the sampling parameter[s] can be evaluated to determine if a particular sampling parameter is interfering with a result. For example, consider the following hypothetical scenario. A result does not accurately provide for a determination of the physiological status of the user (i.e., the user is not suffering from or at risk for hypoglycemia). When the sampling parameters associated with the result are examined, it is determined that the relative humidity was over 30% and the time was 10:00 AM. In additional instances where a result did not accurately provide for a determination of the physiological status of the user, it was determined that the relative humidity was over 30% and that the time was 1:00 PM. In this hypothetical scenario, relative humidity of 30% or greater may be determined to be a sampling parameter that negatively impacts a result, while the time at which the result was determined may be determined to be a sampling parameter that does not negatively impact a result.

Exemplary Mode of Operation

Figure 5:
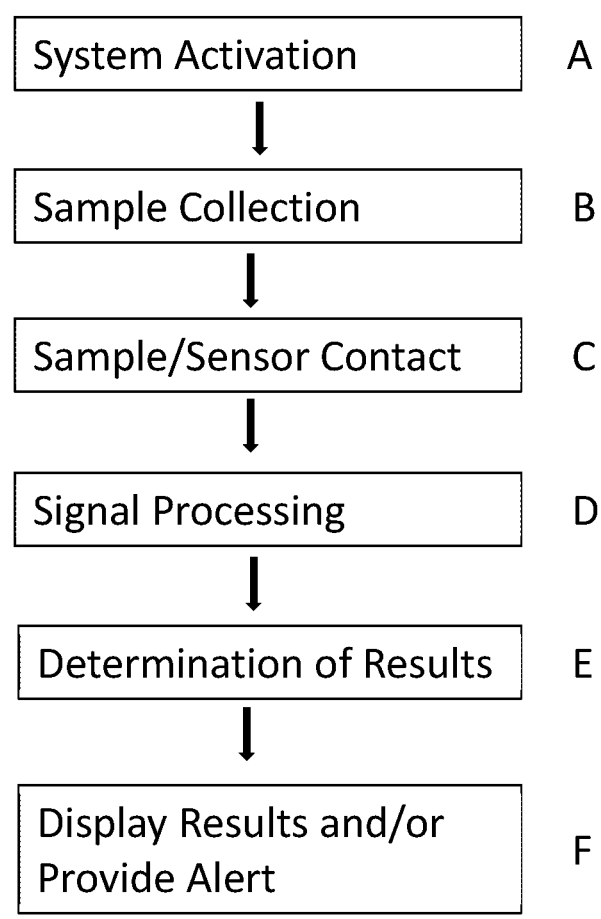
FIG. 5 describes an exemplary mode of operation of the device of FIG. 2.

Referring now also to FIG. 5, a flow chart illustrating operation of wearable device 1 is shown. FIG. 5 illustrates the wearable device 1 of FIG. 2 in operation, although the description is applicable to the other embodiments of the wearable device 1 described. FIG. 5 illustrates a test for hypoglycemia using ambient air as the sample and VOCs as the analyte, although other conditions may be tested, other samples used and other analytes determined. A test begins (step A) with the controller 60 activating the sensor system 50 of the wearable device 1. The controller may be programmed to begin a test on a predetermined schedule or as directed by a user (such as through a user input 100 on the wearable device 1). After the sensor system 50 is activated, the controller activates the pump assembly 90 to draw the sample of ambient air into the chamber 30 via the inlet passages 20a and 20b (or alternatively open or provide access to an inlet). The ambient air passes through membranes 25 to filter large particulates and/or to remove or reduce moisture content in the ambient air (step B).

The sample is then exposed to/contacted with the sensor system 50. The sensor system 50 detects the VOCs present in the sample to provide a signal (i.e., data) when a VOC to which a sensor of the sensor system 50 is responsive is present in the sample. After the sample is contacted with the sensor system 50, the data regarding the analyte is transferred from the sensor to the data module 52 (or alternatively directly to the processor, memory or separate computing device other suitable). The controller 60 acquires the signal from the data module 52 by calling or activating the data module 52. The controller 60 then processes the signal according to instructions provided in the controller 60 to provide a result (which may be the presence, concentration and/or amount of one or more VOCs) (step D). From a result, the controller 60 may optionally determine a status of hypoglycemia. The status can be any status desired, for example, "normal", "borderline", or "hypoglycemic". The data, results, and/or status is optionally saved by the controller to a memory (which may be a spate memory or a part of the controller) (step E). Alternatively, the signal may be processed by a separate computing device as described herein. The controller may use the data, results, and or status to provide an alert to the user through a notification module 102 the wearable device 1, such as for example a visible alert (for example, through LED indicators), an audible alert (for example, an audible alarm), or a tactile alert (for example, a vibrational alarm). Alternatively, the data, results, and/or status are transmitted form the controller 60, via the wireless module 70, to one or more receiving devices (i.e., a separate computing device). The receiving devices may display the data, results, and/or status and/or provide an alert to the user as described above. In addition, in some embodiments, the data, results, and/or status and/or alerts can be both provided locally and wirelessly transmitted to a receiving device (step F).

The transmitted data, results, and/or status can be transmitted to the user and/or the user's selected caregiver, family member or any other desired recipient. The communication between the wearable device 1 and a receiving device can be encrypted as described herein to ensure privacy of the transmitted data, results, and/or status. The receiving device can be programmed to include an application that serves as the interface for observing and analyzing the information transmitted and to provide a display of the transmitted information over time to provide the user a history of the transmitted information for selected time frames as well as compare data, results, and/or status over different timeframes.

In summary, the controller can collect the data generated by the sensor system, process the data to provide data, results, and/or status, and/or store that data, results, and/or status in memory. The data, results, and/or status can be displayed locally on the wearable device and/or on a receiving device. Alerts may be provided locally through the wearable device and/or the receiving device. The data, results, and/or status and/or alerts may be provided to the user as well as the user's caregiver, family members, or other desired recipients.

IN preferred embodiments, the non-invasive monitoring is accomplished without requiring the user to provide a direct sample to the device (for example, exhaling directly into the device).

In preferred embodiments, the non-invasive monitoring is accomplished without requiring the user to exhale into the device to initiate the monitoring process, to complete the monitoring process, determine a result of the monitoring process, and/or view such results.

In preferred embodiments, the non-invasive monitoring is accomplished without requiring an action of the user to initiate the monitoring process, to complete the monitoring process, determine a result of the monitoring process, and/or view such results.

It should be understood that the methods and apparatuses described above are only exemplary and do not limit the scope of the present disclosure or claims, and that various modifications could be made by those skilled in the art that would fall within the scope of the present disclosure and claims. The sensors described herein can be used with various monitoring applications in addition to medical applications. Although specific hardware elements are described, it will be apparent to those of ordinary skill in the art that equivalent elements can be used, and that the construction can be re-configured to reduce the number of components in the system.

Methods of Use

The described wearable device may be used by a subject to monitor one or more analytes. Such monitoring may be used to allow a user to monitor his/her health status over time and avoid suffering from a given disease or condition. As the wearable device of the present disclosure provides information regarding the analyte without requiring the user to take steps to initiate or complete the monitoring process, the risk of non-compliance with analyte monitoring is decreased, with a resulting benefit to the health of the user.

The wearable device of the present disclosure may be used in many way. In one embodiment, the present disclosure provides for a method of evaluating a physiological status of a user by non-invasive monitoring of an analyte in a sample from the user, the method comprising: a) providing a wearable device of the present disclosure wherein the user wears the device; b) exposing a sensor system of the wearable device to the sample; c) detecting the analyte via the sensor system, wherein the sensor system generates a signal in the presence of the analyte; d) analyzing the signal to determine the presence, amount and/or concentration of the analyte to produce a result; e) and optionally (i) providing the result to the user; (ii) alerting the user of the result; and/or (iii) notifying the user if the result is within an acceptable range or outside of an acceptable range for the physiological status.

In another embodiment, the present disclosure provides for a method for determining if a user is suffering from, likely to suffer from, or in danger of suffering from a disease or condition by non-invasive monitoring of an analyte in a sample from the user, the method comprising: a) providing a wearable device of the present disclosure wherein the user wears the device; b) exposing a sensor system of the wearable device to the sample; c) detecting the analyte via the sensor system, wherein the sensor system generates a signal in the presence of the analyte; d) analyzing the signal to determine the presence, amount and/or concentration of the analyte to produce a result; e) and optionally (i) providing the result to the user; (ii) alerting the user of the result; and/or (iii) w notifying the user if the result is within an acceptable range or outside of an acceptable range for the disease of condition.

In one embodiment, when a physiological status is being evaluated, the physiological status is hypoglycemia. In one embodiment, when a physiological status is being evaluated, the physiological status is an infection, a respiratory infection, a urinary infection, a gastrointestinal infection, obesity, diabetes, type I diabetes, or type II diabetes.

In certain aspects of the methods described herein, the non-invasive monitoring is accomplished without requiring the user to provide a direct sample to the device (for example, exhaling directly into the device). In certain aspects of the methods described herein, the non-invasive monitoring is accomplished without requiring the user to exhale into the device to initiate the monitoring process, to complete the monitoring process, determine a result of the monitoring process, and/or view such results. In certain aspects of the methods described herein, the non-invasive monitoring is accomplished without requiring an action of the user to initiate the monitoring process, to complete the monitoring process, determine a result of the monitoring process, and/or view such results.

The wearable device may be any device described herein. The sample may be any sample described herein. In one embodiment, the sample is an indirect sample. An indirect sample is a sample that is not introduced directly into the device by a user (for example, a user breathing through a tube into an inlet port of the device). In one embodiment, the sample is co-mingled with the ambient environment of the user (for example, ambient air) before being introduced into the device. In a particular embodiment, the sample is ambient air that surrounds the wearable device and the user. When the sample is ambient air, the analyte originates from or is derived from the user of the wearable device and becomes mixed with ambient air such that the target analyte is contained in the ambient air surrounding the user.

The analyte may be any analyte described herein and may be present in the sample at any concentration described herein (for example, at a concentration between 1 part per ppb and 10 ppm). In certain embodiments, the analyte is a VOC. In certain embodiments, the analyte is a VOC and the physiological status is hyperglycemia. In certain embodiments, the physiological status is hypoglycemia and the VOC detected is: (1) acetone, methyl nitrate, pentyl nitrate (for example, 2-pentyl nitrate), ethanol, methanol, propanol, methane, propane, ethyl benzene, isoprene, O-xylene, M/P-xylene, formaldehyde, acetaldehyde, or any combination of the foregoing; (2) acetone, methyl nitrate, pentyl nitrate (for example, 2-pentyl nitrate), ethanol, methanol, propanol, methane, propane, ethyl benzene, isoprene or any combination of the foregoing; (3) acetone and methyl nitrate, pentyl nitrate (for example, 2-pentyl nitrate), ethanol, methanol, propanol, methane, propane, ethyl benzene, isoprene, O-xylene, M/P-xylene, formaldehyde, acetaldehyde, or any combination of the foregoing; (4) acetone and methyl nitrate, pentyl nitrate (for example, 2-pentyl nitrate), ethanol, methanol, propanol, methane, propane, ethyl benzene, isoprene, or any combination of the foregoing; (5) acetone and pentyl nitrate (for example, 2-pentyl nitrate), methanol, propane, isoprene, or any combination of the foregoing; (6)

ethanol and methyl nitrate, pentyl nitrate (for example, 2-pentyl nitrate), acetone, methanol, propanol, methane, propane, ethyl benzene, isoprene, O-xylene, M/P-xylene, formaldehyde, acetaldehyde, or any combination of the foregoing; (7) ethanol and methyl nitrate, pentyl nitrate (for example, 2-pentyl nitrate), ethanol, acetone, propanol, methane, propane, ethyl benzene, isoprene, or any combination of the foregoing; (8) ethanol and methyl nitrate, ethyl benzene, or any combination of the foregoing; (9) isoprene and acetone, methyl nitrate, pentyl nitrate (for example, 2-pentyl nitrate), ethanol, methanol, propanol, methane, propane, ethyl benzene, O-xylene, M/P-xylene, formaldehyde, acetaldehyde, or any combination of the foregoing; 10) ethanol, methyl nitrate, and ethyl benzene; or 11) acetone, pentyl nitrate (for example, 2-pentyl nitrate), methanol, propane, and isoprene.

What is claimed is:

1. A method of evaluating a physiological status of a user by non-invasive monitoring of at least one analyte in samples from the user containing the at least one analyte, the method comprising:
   a. providing a wearable device, wherein the user wears the device;
   b. exposing a sensor system of the wearable device to a training sample from the user;
   c. detecting the at least one analyte in the training sample via the sensor system, wherein the sensor system generates a signal in the presence of the at least one analyte;
   d. analyzing the signal to determine the presence, amount, or concentration of the at least one analyte in the training sample;
   e. testing the user for a physiological status by an independent means;
   f. providing the test result and matching the test result to the determined presence, amount, or concentration of the at least one analyte in the training sample;
   g. training the wearable device based on at least the matched test result;
   h. exposing the sensor system of the wearable device to a monitoring sample from the user;
   i. detecting the at least one analyte in the monitoring sample via the sensor system;
   j. analyzing the signal to determine the presence, amount, or concentration of the at least one analyte in the monitoring sample; and
   k. determining the physiological status of the user based on at least the training and the determined presence, amount, or concentration of the at least one analyte in the monitoring sample.

2. The method of claim 1, wherein the training sample is an indirect sample.

3. The method of claim 1, wherein the training sample is ambient air comprising at least one analyte emanating from the user.

4. The method of claim 1, wherein the physiological status is hypoglycemia, an infection, a respiratory infection, a urinary infection, a gastrointestinal infection, obesity, diabetes, type I diabetes, or type II diabetes.

5. The method of claim 1, wherein the analyte is a volatile organic compound.

6. The method of claim 1, wherein the exposing the sensor system to samples is accomplished without requiring the user to exhale directly into the device.

7. The method of claim 1, wherein the exposing the sensor system to samples is accomplished without requiring the user to exhale into the device and the determining the physiological status is accomplished without requiring the user to initiate the exposure to the monitoring sample, to complete the monitoring process, to determine a result of the monitoring process, or view the result.

8. The method of claim 1, wherein 2 to 5 analytes are detected.

9. The method of claim 1, wherein a single analyte is detected.

10. The method of claim 1, wherein the analyte is present in the training sample at a concentration between 1 part per billion and 10 parts per million.

11. The method of claim 1, wherein the analyte is a volatile organic compound and is present in the training sample at a concentration between 1 part per billion and 10 parts per million.

12. The method of claim 1, wherein the analyte is a volatile organic compound and the physiological status is hyperglycemia.

13. The method of claim 12, wherein the volatile organic compound is:
   a. acetone and one or more additional volatile organic compounds;
   b. ethanol and one or more additional volatile organic compounds; or
   c. isoprene and one or more additional volatile organic compounds.

14. The method of claim 13, wherein the volatile organic compound is acetone, methyl nitrate, pentyl nitrate, ethanol, methanol, propanol, methane, propane, ethyl benzene, isoprene, or any combination of the foregoing.

15. The method of claim 13, wherein the volatile organic compound is acetone and methyl nitrate, pentyl nitrate, ethanol, methanol, propanol, methane, propane, ethyl benzene, isoprene, O-xylene, M/P-xylene, formaldehyde, acetaldehyde, or any combination of the foregoing.

16. The method of claim 13, wherein the volatile organic compound is ethanol and methyl nitrate, pentyl nitrate, acetone, methanol, propanol, methane, propane, ethyl benzene, isoprene, O-xylene, M/P-xylene, formaldehyde, acetaldehyde, or any combination of the foregoing.

17. The method of claim 13, wherein the volatile organic compound is isoprene and acetone, methyl nitrate, pentyl nitrate, ethanol, methanol, propanol, methane, propane, ethyl benzene, O-xylene, M/P-xylene, formaldehyde, acetaldehyde, or any combination of the foregoing.

18. The method of claim 13, wherein the volatile organic compound is one or more of ethanol, methyl nitrate, or ethyl benzene.

19. The method of claim 13, wherein the volatile organic compound is one or more of acetone, pentyl nitrate, methanol, propane, or isoprene.

20. The method of claim 1, wherein the exposing the sensor system to a monitoring sample is accomplished without requiring an action of the user to initiate the monitoring process, to complete the monitoring process, to determine a result of the monitoring process, or view a result.

21. The method of claim 13, wherein the volatile organic compound is acetone, methyl nitrate, pentyl nitrate, ethanol, methanol, propanol, methane, propane, ethyl benzene, isoprene, O-xylene, M/P-xylene, formaldehyde, acetaldehyde, or any combination of the foregoing.

* * * * *